United States Patent
Laidlaw et al.

(10) Patent No.: US 8,170,305 B2
(45) Date of Patent: May 1, 2012

(54) QUANTITATIVE TRACT-OF-INTEREST METRICS FOR WHITE MATTER INTEGRITY BASED ON DIFFUSION TENSOR MRI DATA

(75) Inventors: David H Laidlaw, Barrington, RI (US); Song Zhang, Starkville, MS (US); Stephanie Yat-Lin Lee, Needham, MA (US); Stephen Correia, Cranston, RI (US)

(73) Assignee: Brown University, Providence, RI (US)

( * ) Notice: Subject to any disclaimer, the term of this patent is extended or adjusted under 35 U.S.C. 154(b) by 1162 days.

(21) Appl. No.: 11/975,416

(22) Filed: Oct. 19, 2007

(65) Prior Publication Data

US 2008/0205733 A1 Aug. 28, 2008

Related U.S. Application Data

(60) Provisional application No. 60/852,922, filed on Oct. 19, 2006.

(51) Int. Cl.
*G01N 31/00* (2006.01)

(52) U.S. Cl. ........ 382/128; 382/154; 324/309; 324/312; 345/419; 345/424; 345/442; 600/410; 702/28

(58) Field of Classification Search .................. 382/128, 382/154; 324/309, 312; 345/419, 424, 442; 600/410; 702/28
See application file for complete search history.

(56) References Cited

U.S. PATENT DOCUMENTS

| | | | |
|---|---|---|---|
| 5,812,691 A * | 9/1998 | Udupa et al. .................. 382/128 |
| 6,345,112 B1 * | 2/2002 | Summers et al. ............. 382/128 |
| 6,591,004 B1 * | 7/2003 | VanEssen et al. ............. 382/154 |
| 7,034,531 B1 * | 4/2006 | Tuch et al. .................... 324/309 |
| 7,355,597 B2 * | 4/2008 | Laidlaw et al. ............... 345/419 |
| 7,602,180 B2 * | 10/2009 | McGraw ....................... 324/307 |
| 7,672,790 B2 * | 3/2010 | McGraw et al. ................ 702/19 |
| 7,881,878 B2 * | 2/2011 | Burrus et al. .................. 702/28 |
| 7,928,728 B2 * | 4/2011 | Wedeen ........................ 324/309 |
| 2003/0234781 A1 * | 12/2003 | Laidlaw et al. ............... 345/419 |
| 2008/0205733 A1 * | 8/2008 | Laidlaw et al. ............... 382/131 |
| 2010/0135560 A1 * | 6/2010 | Embleton et al. ............. 382/131 |

OTHER PUBLICATIONS

"From diffusion tractography to quantitative white matter tract measures: a reproducibility study", Ciccarelli, O., et al, NeuroImage 18 (2003), 348-359.

"Exploring Connectivity of the Brain's White Matter with Dynamic Queries", Sherbondy, A., et al, IEEE Transactions on Visualization and Computer Graphics, vol. 11, No. 4, Jul./Aug. 2005.

(Continued)

*Primary Examiner* — David A Vanore
(74) *Attorney, Agent, or Firm* — Harrington & Smith

(57) ABSTRACT

The exemplary embodiments of this invention relate at least in part to a method, apparatus and system to characterize white matter, such as for detecting a presence of a white matter impairment. An exemplary method to characterize white matter includes identifying at least one tract of interest (TOI) in the brain of a subject of interest, the tract of interest having a set of streamtubes representing white matter fibers; determining a set of quantitative tractography metrics associated with the tract of interest, the set of quantitative tractography metrics having a plurality of members; and comparing at least one member of the determined set of quantitative tractography metrics to a corresponding member of a reference set of quantitative tractography metrics, or comparison of one TOI in a single subject or group of subjects and other TOI in the same subject(s).

25 Claims, 7 Drawing Sheets

OTHER PUBLICATIONS

"Visualizing Diffusion Tensor MR Images Using Streamtubes and Streamsurfaces", Zhang, S., et al, IEEE Transactions on Visualization and Computer Graphics, vol. 9, No. 4, Oct./Dec. 2003.

"DTI tractography based parcellation of white matter: Appication to the mid-sagittal morphology of corpus callosum", Hao Huang et al., NeuroImage 26 (2005), pp. 195-205.

"Classification and Quantification of Neuronal Fiber Pathways Using Diffusion Tensor MRI", Zhaohua Ding et al., Magnetic Resonance in Medicine 49, (2003), pp. 716-721.

"Detection of age-dependent brain injury in a mouse model of brain amyloidosis associated with Alzheimer's disease using magnetic resonance diffusion tensor imaging", Shu-Wei Sun et al., Science Direct, Experimental Neurology 191 (2005), pp. 77-85.

"Color Schemes to Represent the Orientation of Anisotropic Tissues From Diffusion Tensor Data: Application to White Matter Fiber Tract Mapping in the Human Brain", Sinisa Pajevic et al., Magnetic Resonance in Medicine 42 (1999), pp. 526-540.

"Diffusion tractography based group mapping of major white-matter pathways in the human brain", O. Ciccarelli et al., Science Direct, NeuroImage 19 (2003), pp. 1545-1555.

"Estimating Distributed Anatomical Connectivity Using Fast Marching Methods and Diffusion Tensor Imaging", Geoffrey J.M. Parker et al., IEEE 2002, pp. 505-512.

"In Vivo Three-Dimensional Reconstruction of Rat Brain Axonal Projections by Diffusion Tensor Imaging", Rong Xue et al., Magnetic Resonance in Medicine 42, (1999), pp. 1123-1127.

"Initial Demonstration of in Vivo Tracing of Axonal Projections in the Macaque Brain and Comparison with the Human Brain Using Diffusion Tensor Imaging and Fast Marching Tractography", Geoffrey J. M. Parker et al., NeuroImage 15, (2002), pp. 797-809.

"Macroscopic Orientation Component Analysis of Brain White Matter and Thalamus Based on Diffusion Tensor Imaging", Setsu Wakana, et al., Magnetic Resonance in Medicine 53 (2005, pp. 649-657.

"MR Diffusion Tensor Spectroscopy and Imaging", Peter J. Basser et al., Biophysical Journal, vol. 66, Jan. 1994, pp. 259-267.

"The basis of anisotropic water diffusion in the nervous system—a technical review", Christian Beaulieu, NMR in Biomedicine, 2002, pp. 435-455.

"Tracing Fibre Tracts Using Fast Marching", G.J.M. Parker, Proceedings of the International Society of Magnetic Resonance in Medicine 85, (2000), 1 pg.

* cited by examiner

TABLE 1. METRIC DEFINITION

| ABBREVIATION | DEFINITION |
|---|---|
| TL | TOTAL LENGTH: THE TOTAL SUMMED LENGTH OF ALL STREAMTUBES IN THE TRACT OF INTEREST |
| TWL | TOTAL WEIGHTED LENGTH: THE TOTAL SUMMED LENGTH OF ALL STREAMTUBES IN THE TRACT OF INTEREST AFTER WEIGHTING EACH STREAMTUBE BY ITS AVERAGE LINEAR ANISOTROPY |
| NS | NUMBER OF STREAMTUBES: THE TOTAL NUMBER OF STREAMTUBES IN THE TRACT OF INTEREST |
| NTL | NORMALIZED TOTAL LENGTH: TL NORMALIZED FOR ESTIMATED INTRACRANIAL VOLUME |
| NTWL | NORMALIZED TOTAL WEIGHTED LENGTH: TWL NORMALIZED BY INTRACRANIAL VOLUME |
| NNS | NORMALIZED NUMBER OF STREAMTUBES: THE TOTAL NUMBER OF STREAMTUBES CORRECTED FOR ESTIMATED INTRACRANIAL VOLUME |
| AL | AVERAGE LENGTH: THE TOTAL SUMMED LENGTH OF ALL STREAMTUBES DIVIDED BUY THE NUMBER OF STREAMTUBES IN A TRACT OF INTEREST |

FIG.1

TABLE 2: RESULTS OF THE REPRODUCIBILITY STUDY (MEAN ± SD) AND COEFFICIENT OF VARIANCE (COV; MEANS AND SD ROUNDED)

| SEED | NS | TL(mm) | TWL(mm) |
|---|---|---|---|
| 1.70 mm$^3$ | 7895 ± 11 COV=.1% | 108978 ± 844 COV=.8% | 26874 ± 256 COV=1.0% |
| 0.85 mm$^3$ | 11856 ± 28 COV=.2% | 138752 ± 823 COV=.8% | 33639 ± 245 COV=.9% |
| 0.64 mm$^3$ | 13406 ± 40 COV=.3% | 151180 ± 703 COV=.8% | 36381 ± 157 COV=.4% |

NOTE: CELL VALUES ARE CALCULATED FROM SEVEN MODELS AT EACH SEEDING PARAMETER

FIG.2

TABLE 3: GROUP COMPARISON, WHOLE BRAIN CORRECTED FOR AGE

| METRIC | HEALTHY CONTROLS (n=18) | VCI (n=15) | F(1,30) | p |
|---|---|---|---|---|
| WHOLE BRAIN | | | | |
| TL(mm) | 396453 ± 84619 | 327370 ± 97501 | 7.71 | .009 |
| TWL(mm) | 103883 ± 24499 | 80186 ± 26602 | 10.20 | .003 |
| NS | 12647 ± 2076 | 11385 ± 2571 | 5.42 | .027 |
| NTL(mm) | 398065 ± 91649 | 329330 ± 97363 | 7.59 | .010 |
| NTWL(mm) | 104225 ± 25884 | 80812 ± 26859 | 9.95 | .004 |
| NNS | 12690 ± 2281 | 11466 ± 2700 | 4.90 | .035 |
| AL(mm) | 31 ± 3 | 28 ± 3 | 8.46 | .007 |
| TRANSCALLOSAL FIBERS | | | | |
| TL(mm) | 46462 ± 13521 | 32526 ± 14969 | 14.00 | .001 |
| TWL(mm) | 15834 ± 4610 | 10399 ± 5304 | 16.23 | <.001 |
| NS | 821 ± 163 | 650 ± 214 | 10.87 | .003 |
| NTL(mm) | 46668 ± 14173 | 32983 ± 15394 | 13.25 | .001 |
| NTWL(mm) | 15901 ± 4908 | 10581 ± 5478 | 15.21 | .001 |
| NNS | 822 ± 164 | 658 ± 214 | 10.19 | .003 |
| ATL(mm) | 56 ± 7 | 48 ± 9 | 15.07 | .001 |

FIG.4A

| LEFT CINGULUM BUNDLE ||||| 
|---|---|---|---|---|
| TL(mm) | 3261 ± 1416 | 3564 ± 2233 | 0.07 | .799 |
| TWL(mm) | 888 ± 429 | 964 ± 700 | 0.05 | .832 |
| NS | 57 ± 21 | 60 ± 27 | 0.01 | .755 |
| NTL(mm) | 3315 ± 1551 | 3573 ± 2324 | 0.03 | .860 |
| NTWL(mm) | 904 ± 472 | 971 ± 739 | 0.03 | .876 |
| NNS | 60 ± 23 | 60 ± 28 | 0.15 | .705 |
| AL(mm) | 54 ± 8 | 56 ± 11 | 0.43 | .520 |
| RIGHT CINGULUM BUNDLE ||||| 
| TL(mm) | 3177 ± 1238 | 3090 ± 1615 | 0.21 | .652 |
| TWL(mm) | 939 ± 396 | 864 ± 504 | 0.57 | .462 |
| NS | 57 ± 20 | 55 ± 22 | 0.47 | .500 |
| NTL(mm) | 3165 ± 1208 | 3101 ± 1542 | 0.21 | .654 |
| NTWL(mm) | 963 ± 395 | 868 ± 485 | 0.56 | .462 |
| NNS | 57 ± 19 | 55 ± 21 | 0.47 | .500 |
| AL(mm) | 55 ± 8 | 53 ± 9 | 0.22 | .644 |

FIG.4B

TABLE 4. PARTIAL CORRELATIONS (CONTROLLED FOR AGE) BETWEEN
COGNITIVE TESTS AND NTWL IN WHOLE BRAIN TOI
(WHOLE SAMPLE, n= 33)

| COGNITIVE TEST | NTWL | |
|---|---|---|
| | r | p |
| TMT-A | -.415 | .020 |
| TMT-B | -.432 | .015 |
| BNT | .187 | .313 |

TMT-A = TRAIL MAKING TEST PART A (A TEST OF PSYCHOMOTOR PROCESSING SPEED)
TMT-B = TRAIL MAKING TEST PART B (A TEST OF EXECUTIVE FUNCTION, SPECIFICALLY COGNITIVE SET SWITCHING)
BNT = BOSTON NAMING TEST (A MEASURE OF CONFRONTATIONAL NAMING)

FIG.5

QUANTITATIVE TRACT-OF-INTEREST METRICS FOR WHITE MATTER INTEGRITY BASED ON DIFFUSION TENSOR MRI DATA

CLAIM OF PRIORITY FROM A COPENDING US PROVISIONAL PATENT APPLICATION

This patent application claims priority under 35 USC 119 (e) from U.S. Provisional Patent Application No. 60/852,922, filed Oct. 19, 2006, the disclosure of which is incorporated by reference herein in its entirety.

FIELD OF THE INVENTION

The exemplary embodiments of this invention relate generally to systems, methods and apparatus for processing data generated by an imaging system, such as a magnetic resonance imaging (MRI) system.

BACKGROUND

Diffusion tensor imaging (DTI) is a magnetic resonance imaging (MRI) technique that measures the directionally dependent rate of water self-diffusion in each image voxel. These measures are in the form of a second-order diffusion tensor (Basser, P. J., Mattiello, J., & LeBihan, D. (1994), MR diffusion tensor spectroscopy and imaging. Biophys J, 66(1), 259-267), which can be decomposed into three non-negative eigenvalues and three eigenvectors that describe the magnitude and orientation of water diffusion in each image voxel. Water diffusion in cerebral white matter tends to be anisotropic due to the highly linear organization of white matter fibers. That is, water will preferentially diffuse more rapidly along white matter tracts because physical barriers such as axonal walls restrict water movement in other directions (see Beaulieu, C. (2002), The basis of anisotropic water diffusion in the nervous system—a technical review, NMR Biomed, 15(7-8), 435-455, and see also Sun, S. W., Song, S. K., Harms, M. P., Lin, S. J., Holtzman, D. M., Merchant, K. M. (2005), Detection of age-dependent brain injury in a mouse model of brain amyloidosis associated with Alzheimer's disease using magnetic resonance diffusion tensor imaging. Exp Neurol, 191(1), 77-85). Medical conditions, such as subcortical ischemic injury, inflammation, neurodegenerative diseases, and traumatic brain injury cause changes in the organization of white matter pathways, often including reductions in its linearity, with corresponding changes in anisotropy as well as the speed and direction of diffusion. DTI is sensitive to these changes making it a powerful in vivo imaging tool for studying the microstructural integrity of cerebral white matter.

The majority of studies using DTI to assess white matter microstructure in clinical samples have been based on two-dimensional greyscale maps of scalar values such as mean diffusivity (MD), a measure of the magnitude of diffusion in each image voxel, and fractional anisotropy (FA), a measure of the extent to which that diffusion is directionally restricted. Generally, these basic scalar measures are derived from the eigenvalues of the multi-valued tensor data and do not incorporate eigenvector information. The scalar values in each image voxel are then mapped to two-dimensional greyscale images. An exception is the use of eigenvector information to produce two-dimensional FA maps in which fiber orientation is mapped to color (for example, see Pajevic, S., & Pierpaoli, C. (1999), Color schemes to represent the orientation of anisotropic tissues from diffusion tensor data: Application to white matter fiber tract mapping in the human brain, Magn Reson Med, 42(3), 526-540, and also Wakana, S., Nagae-Poetscher, L. M., Jiang, H., van Zijl, P., Golay, X., & Mori, S. (2005), Macroscopic orientation component analysis of brain white matter and thalamus based on diffusion tensor imaging, Magn Reson Med, 53(3), 649-657).

Of particular interest to the embodiments of the invention described herein is Westin, C. F., Peled, S., Gubjartsson, H., Kikinis, R., & Jolesz, F. (1997), Geometrical diffusion measures for MRI from tensor basis analysis, Paper presented at the International Society for Magnetic Resonance in Medicine, Vancouver, Canada, where a linear anisotropy measure is shown to be a geometric parameter that is descriptive of diffusion mainly being in the direction of the largest eigenvalue.

Tractography methods complement scalar methods by providing detailed information about the orientation and curvature of white matter pathways within the brain. Tractography methods utilize both the tensor eigenvalues and the eigenvectors to calculate trajectories generally in the direction of the fastest diffusion. The trajectories are then portrayed graphically using curved lines (see Xue, R., van Zijl, P. C., Crain, B. J., Solaiyappan, M., & Mori, S. (1999), In vivo three-dimensional reconstruction of rat brain axonal projections by diffusion tensor imaging, Magn Reson Med, 42(6), 1123-1127) or by using glyphs, such as hyperstreamlines, which were initially proposed by Delmarcelle and Hesselink (1993) as a means of visualizing other types of second-order tensor fields, and then subsequently applied to DT-MRI data by Zhang et al. (Zhang, S., Demiralp, C., & Laidlaw, D. (2003), Visualizing diffusion tensor MR images using streamtubes and streamsurfaces, IEEE Transactions on Visualization and Computer Graphics, 9(4), 454-462). To date, tractography methods have gained the widest acceptance in neuroscience studies that explore white matter connectivity, the effects of pathologies on connectivity, and improvements in data acquisition and visualization methods.

Only a few preliminary methodological studies have explored the utility of combining tractography with quantitative scalar measures (i.e., "quantitative tractography") for clinical research, where group comparisons are important. For example, Ciccarelli et al. (Ciccarelli, O., Parker, G. J., Toosy, A. T., Wheeler-Kingshott, C. A., Barker, G. J., Boulby, P. A., et al. (2003a), From diffusion tractography to quantitative white matter tract measures: A reproducibility study, Neuroimage, 18(2), 348-359) studied the reproducibility of tract-"normalized" volume (NV) and FA in three white matter pathways traced by a fast marching tractography (FMT) algorithm (see Parker, G. J. (2000), Tracing fibre tracts using fast marching, Proceedings of the International Society of Magnetic Resonance in Medicine, 85; Parker, G. J., Stephan, K. E., Barker, G. J., Rowe, J. B., MacManus, D. G., Wheeler-Kingshott, C. A., et al. (2002a), Initial demonstration of in vivo tracing of axonal projections in the macaque brain and comparison with the human brain using diffusion tensor imaging and fast marching tractography, Neuroimage, 15(4), 797-809; and Parker, G. J., Wheeler-Kingshott, C. A., & Barker, G. J. (2002b), Estimating distributed anatomical connectivity using fast marching methods and diffusion tensor imaging, IEEE Trans Med Imaging, 21(5), 505-512). The results (Ciccarelli et al., 2003a) showed variability in measures of tract volume and fractional anisotropy across different fiber bundles, suggesting that fiber organization has an impact on the reproducibility of tractography algorithms. Ciccarelli et al. (Ciccarelli, O., Toosy, A. T., Parker, G. J., Wheeler-Kingshott, C. A., Barker, G. J., Miller, D. H., et al. (2003b), Diffusion tractography based group mapping of major white-matter pathways in the human brain, Neuroimage, 19(4), 1545-1555) also examined the extent of intersubject variability in the anterior corpus callosum, optic radiations, and pyramidal tracts. They found that the tractography maps corresponded well to known anatomy and that there was greater intersubject variability at the terminal ends of tracts adjacent to cerebral cortex, but lower variability in the core of tracts, and no right-left differences in variability. Ding et al. (2003) (Ding, Z., Gore, J. C., & Anderson, A. W. (2003), Classification and quantification of neuronal fiber pathways using diffusion tensor MRI. Magn Reson Med, 49(4), 716-721) also demonstrated good reproducibility of tractography-based metrics such as curvature, torsion, parallel diffusivity, and perpendicular diffusivity along bundle length. Huang et al. (2005) (Huang, H., Zhang, J., Jiang, H., Wakana, S., Poetscher, L., Miller, M. I., et al. (2005), DTI tractography based parcellation of white matter: Application to the mid-sagittal morphology of corpus callosum, Neuroimage, 26(1), 195-205) have also used quantitative methods for parcellating projections from the corpus callosum to cortical regions. Each of these studies demonstrated the utility of using quantitative tractography.

However, prior to this invention researchers were limited in their ability to pose and address questions concerning the integrity of specific white matter pathways in their entirety (i.e., following the trajectory of the pathway in all three dimensions), and their relationship to cognitive and behavioral changes in a variety of conditions affecting cerebral white matter. Such questions cannot be adequately addressed using conventional region-of-interest approaches with scalar DTI maps. While some earlier quantitative tractography work described above may address some of these limitations, it does not do so adequately.

It is noted that Ciccarelli et al. (Ciccarelli, O., Parker, G. J., Toosy, A. T., Wheeler-Kingshott, C. A., Barker, G. J., Boulby, P. A., et al. (2003a), From diffusion tractography to quantitative white matter tract measures: A reproducibility study, Neuroimage, 18(2), 348-359), discuss normalizing tract volume using the total intercranial volume (see page 352, left column) in a determination of connectivity.

SUMMARY OF THE EXEMPLARY EMBODIMENTS

The foregoing and other problems are overcome, and other advantages are realized, in accordance with the non-limiting and exemplary embodiments of this invention.

In a first aspect thereof the exemplary embodiments of this invention provide a method to characterize white matter, comprising identifying at least one tract of interest (TOI) in the brain image of a subject of interest, the tract of interest comprising a set of streamtubes representing white matter fibers; determining a set, of quantitative tractography metrics associated with the tract of interest, the set of quantitative tractography metrics comprising a plurality of members; and comparing at least one member of the determined set of quantitative tractography metrics to a corresponding member of a reference set of quantitative tractography metrics.

In another aspect thereof the exemplary embodiments of this invention provide a system configurable to detect a presence of white matter impairment. The system comprises a data processor operable to process data representing white matter fibers in at least one tract of interest (TOI) in the brain image of a subject of interest, and is further operable to determine, such as by calculating, a set of quantitative tractography metrics based on the obtained data. The set of quantitative tractography metrics comprise a plurality of members. The system is further operable to compare at least some members of the determined set of quantitative tractography metrics to a reference set of quantitative tractography metrics obtained from a subject or subjects either having or not having a certain white matter impairment, or obtained from the same subject of interest.

In a further aspect thereof the exemplary embodiments of this invention provide an apparatus to detect a presence of white matter impairment. The apparatus includes means, responsive to data obtained by diffusion MRI imaging of a subject of interest, for generating streamtubes representing white matter fibers in at least one tract of interest (TOI) in the brain image of the subject of interest; means for determining a set of quantitative tractography metrics based on the generated streamtubes, the set comprising a plurality of members at least some of which are indicative of streamtube length; and means for comparing at least some members of the determined set of quantitative tractography metrics to a reference set of quantitative tractography metrics for indicating whether the subject of interest may have a white matter impairment.

In a still further aspect thereof the exemplary embodiments of this invention provide a method that comprises generating, from data obtained by diffusion MRI imaging of a subject of interest, a plurality of streamtubes representing white matter fibers in at least one tract of interest (TOI) in the brain image of the subject of interest. The method further comprises determining a set of quantitative tractography metrics based on the generated streamtubes, the set comprising a plurality of members at least some of which are indicative of streamtube length. The method further comprises comparing at least some members of the determined set of quantitative tractography metrics to a reference set of quantitative tractography metrics obtained from at least one reference subject to characterize the at least one TOI.

In an exemplary and non-limiting embodiment of this invention a plurality of the members of the set of quantitative tractography metrics are length-based, and at least one of the members of the set of quantitative tractography metrics is weighted using a scalar measure.

In an exemplary and non-limiting embodiment of this invention the members of the set of quantitative tractography metrics that are indicative of streamtube length comprise a total length TL of a TOI metric, a total weighted length (TWL) of a TOI metric that is the TL weighted by an average linear anisotropy of streamtubes comprising the TOI, a normalized TL (NTL) metric, a normalized TWL (NTWL) metric, and a metric that is a non-normalized measure of the average length (AL) of streamtubes in the TOI, where the normalized metrics are normalized based on intracranial volume. In the exemplary and non-limiting embodiment of this invention members of the set of quantitative tractography metrics that are not indicative of streamtube length comprise a number of streamtubes (NS) in a TOI metric, and a normalized NS (NNS) metric that is normalized based on intracranial volume.

In an exemplary and non-limiting embodiment the at least one reference subject may comprise one of the subject of interest, at least one reference subject known to have a certain white matter impairment and at least one reference subject not known to have a certain white matter impairment.

In an exemplary and non-limiting embodiment of this invention the method(s) may be performed as a result of the execution of at least one computer program stored on at least one computer readable memory medium.

BRIEF DESCRIPTION OF THE DRAWINGS

FIG. 1 shows a representative table (Table 1) that briefly describes each quantitative tractography metric of an exemplary and non-limiting set of quantitative tractography metrics.

FIG. 2 shows a table (Table 2) that illustrates results of a reproducibility study (mean ±SD) and coefficient of variance (COV).

FIGS. 4A and 4B, collectively referred to as FIG. 4, show a table (Table 3) that tabulates whole brain and transcallosal fibers and right and left cingulum bundles (mean ±SD) for healthy and VCI groups covaried for age.

FIG. 5 shows a table (Table 4) of partial correlations (controlled for age) between cognitive tests and NTL and NTWL in whole brain TOI (whole sample, n=33).

DETAILED DESCRIPTION

Figure 3:
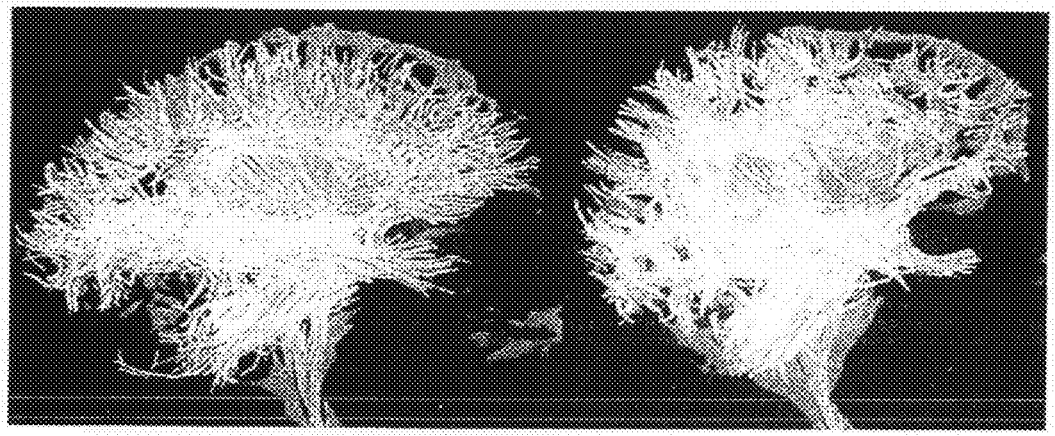
FIG. 3 shows whole brain streamtube models (sagittal view) for a 64-year-old healthy volunteer (left) and a 60-year-old patient with vascular cognitive impairment (VCI) (right), where each streamtube follows a path representative of white matter.

Disclosed herein are novel quantitative diffusion-tensor imaging (DTI) tractography-based metrics for assessing cerebral white matter integrity. Streamtube models representative of underlying cerebral white matter are produced from DTI data for individual subjects. In general, a streamtube provides an ability to visualize a three dimensional (3D) path, where the 3D path may follow white matter, such as by following the direction of fastest diffusion that is obtained from the DTI data set. In general, the 3D paths will be curved paths since they arise from organic structures, such as white matter structures in the brain, and possibly from other nerve cell (or non-nervous tissue) based structures in an organism of interest. For example, the exemplary embodiments of this invention may be used as well with muscle tissue, including the cardiac muscle, as well as with spinal tissue, as non-limiting examples. Thus, while described below primarily in the context of brain tissue, it should be appreciated that the exemplary embodiments are not limited for use with only brain tissue.

The 3D paths may be referred to for simplicity as "curves". A tract-of-interest (TOI) may be considered equivalently as being a selected set of curves, or a selected set of 3D paths, or a selected set of streamtubes, and will generally represent an identifiable assemblage of nerve cells such as, but not limited to, nerve cells that comprise the transcallosal fibers, the left cingulum bundle and the right cingulum bundle. The curves within a given TOI are assumed to be distributed consistently between subjects, as will be the case if they are generated by a procedure such as, but not limited to, the one described by Zhang et al. (2003) (Zhang, S., Demiralp, Q., and Laidlaw, D. H. 2003. Visualizing Diffusion Tensor MR Images Using Streamtubes and Streamsurfaces. *IEEE Transactions on Visualization and Computer Graphics* 9, 4 (October 2003), 454-462). Note that this procedure encompasses calculating numerous streamtubes, and then culling (removing) redundant ones to enhance the consistency between subjects. In this manner a given anatomical structure can be found in multiple subjects and represented by a similar distribution of streamtubes, and a corresponding set of quantitative tractography metrics can be assumed to be approximately consistent between subjects.

It is pointed out, however, that there are individual differences between subjects, and the curves may be very different in some disorders such as schizophrenia.

In a non-limiting embodiment seven (or more) quantitative tractography metrics are calculated in whole brain streamtube models and in three "tracts of interest" (TOIs): namely transcallosal fibers, and the left and right cingulum bundles. The set of quantitative tractography metrics includes the number of streamtubes in a TOI and several metrics based on summed lengths of streamtubes in the TOI. Both raw length metrics are included, as well as metrics weighted for average linear anisotropy and fractional anisotropy and normalized for estimated intracranial volume. The set of quantitative tractography metrics thus derived are tested to determine whether the metrics acquire different values in a group of patients with known white matter disease (i.e., vascular cognitive impairment or VCI) as compared to healthy controls (HC), and whether they correlate with cognitive function as measured by cognitive test performance.

It is noted that some earlier quantitative tractography work (e.g., Ding and Ciccarelli) turn tracts into regions of interest (ROIs), for the most part. The exemplary embodiments of this invention, however, are distinguished from these earlier approaches by operating on the set of curves to calculate metrics, not on the ROIs.

In general, VCI is a form of late-life cognitive impairment related to white matter injury from subcortical ischemic microvascular disease. Patients with VCI typically have impairments that are greater than expected for age in the cognitive domains of processing speed, attention, and executive functioning, and somewhat milder deficits in memory. The level of cognitive impairment and its impact on daily functioning is insufficient to warrant a diagnosis of dementia. The neuroimaging features of VCI include subcortical white matter hyperintensities on T2-weighted MRI and a subcortical lacunar infarction on T1-weighted MRI.

The values associated with tractography-based metrics in accordance with the exemplary embodiments of this invention were found to be significantly lower in a VCI group in whole brain fiber models, and when transcallosal fibers were measured in isolation. It was found that the groups did not differ significantly on any metric when the left and right cingulum bundles were measured in isolation, possibly because VCI does not affect the cingulum bundles. The tractography-based metrics correlated significantly with cognitive functions known to be impacted by white matter abnormalities (e.g., processing speed) but not with cognitive functions more sensitive to cortical disease (e.g., naming). These results provide evidence that these novel quantitative DTI tractography metrics have utility for examining group differences in white matter integrity, and may provide a useful method for tracking longitudinal changes in specific white matter tracts.

The exemplary embodiments of this invention provide a set of novel quantitative tractography metrics for quantifying cerebral white matter integrity in whole brain white matter, and in specific white matter TOIs. The use of these quantitative tractography metrics is based on a basic underlying assumption that declines in white matter integrity result in local changes in diffusion anisotropy and rate. When these changes reach or exceed a certain pre-specified threshold, they cause the tractography algorithm to terminate prematurely. This, in turn, can be expected to have an effect on the length of fibers, and possibly the number of fibers, produced by the tractography algorithm. Thus, patients with disrupted white matter can be expected to have shorter fibers compared to individuals with healthy white matter; and these patients may also have either fewer or greater numbers of fibers depending on the nature of the white matter alterations. The weighted metrics may also distinguish changes even before the aforementioned threshold is reached, making them potentially sensitive to smaller alterations.

The use of these novel quantitative tractography metrics, when coupled with tools for segmenting specific white matter TOIs, permit researchers to pose and address interesting new questions about the integrity of specific white matter pathways in their entirety (i.e., following the trajectory of the pathway in all three dimensions) and their relationship to cognitive and behavioral changes in a variety of conditions affecting cerebral white matter. Such questions cannot be adequately addressed using conventional region-of-interest approaches on scalar DTI maps. One motivating factor in defining these novel quantitative tractography metrics was an incidental observation that tractography models in patients with known vascular white matter disease had fewer and shorter fibers, as compared to age matched controls.

Defined herein are a plurality of novel quantitative tractography metrics. The quantitative tractography metrics are found to be stable across multiple streamtube models derived from a single dataset for a healthy control subject. As an initial and preliminary validity test, a comparison is made of these metrics between a small cohort of patients with known vascular white matter injury (i.e., vascular cognitive impairment, VCI) and a demographically matched cohort of healthy controls. Also examined was the relative sensitivity of these metrics, as compared to fractional anisotropy (FA), to differences in white matter integrity between the groups. VCI provides a good model for assessing the clinical and research utility of quantitative DTI since ischemic white matter injury is associated with a characteristic pattern of increased diffusivity and decreased anisotropy (see Jones, D. K., Lythgoe, D., Horsfield, M. A., Simmons, A., Williams, S. C., & Markus, H. S. (1999), Characterization of white matter damage in ischemic leukoaraiosis with diffusion tensor MRI, Stroke, 30(2), 393-397). These diffusion changes are thought to reflect axonal loss with possible contributions from demyelination, gliosis, or other pathological processes.

Materials and Methods
DTI Acquisition

MRI data was collected on a 1.5T Siemens Symphony™ scanner. Siemens MDDW protocol was used to collect three co-registered sagittal double spin-echo, echo-planar diffusion-weighted volumes of the entire brain. After the initial scan, subsequent acquisitions were spatially offset in the slice direction by 1.7 mm and 3.4 mm. Parameters for each acquisition were as follows: 5 mm thick slices, 0.1 mm inter-slice spacing, 30 slices per acquisition, matrix=128×128, FOV=21.7 cm×21.7 cm, TR=7200, TE=156, no partial echoes, and NEX=3. Bipolar diffusion encoding gradients (b=0, 1000 mm/s$^2$) were applied in 12 non-collinear directions calculated automatically by Siemens software. The reverse polarity during the second echo of the double-spin-echo acquisition unwinds eddy currents that accumulate during the first echo. The total time for the three acquisitions was slightly less than 15 minutes. The three acquisitions were interleaved to achieve 1.7 mm$^3$ resolution images and then up-sampled (equivalent to zero-filling) to 0.85 mm$^3$ isotropic voxels for analysis. The interleaving overlaps the slice profiles of the acquisition making through-plane interpolation possible and produces isotropic voxels which reduces tractography bias related to fiber orientation (Laidlaw, D., Zhang, S., Bastin, M. E., Correia, S., Salloway, S., & Malloy, P. (2004), Ramifications of isotropic sampling and acquisition orientation on DTI analyses (poster), Paper presented at the Twelfth Scientific Meeting and Exhibition, International Society for Magnetic Resonance in Medicine, Kyoto, Japan). It should be noted that typical DTI acquisitions for use with tractography require a higher number of diffusion encoding directions than were used, however 12 directions exceed those used in most studies. As such, more than 12 directions may be used if desired, and if supported by the underlying hardware/software system.

Motion was controlled with the use of a head restraint system provided by the scanner manufacturer, repeated reminders of the importance of remaining still, and other measures to promote subject comfort in the scanner, and all datasets were screened for excessive motion artifact. A post-acquisition motion correction to the data was not used to avoid introducing errors in the tractography models due to misalignment of adjacent voxels with coherent eigenvectors, and it was assumed that the introduction of random jitter in the model aids in accounting for error. Nonetheless, applying motion correction before calculating tensors may be used to improve the reliability and robustness of the results.

Streamtube Generation

Streamtubes are generated using software to calculate tensors and then derive the three principle eigenvalues and eigenvectors for each image voxel after interleaving of three diffusion-weighted images. One suitable embodiment for accomplishing this step is disclosed in: Ahrens, E. T., Laidlaw, D. H., Readhead, C., Brosnan, C. F., Fraser, S. E., & Jacobs, R. E. (1998), MR microscopy of transgenic mice that spontaneously acquire experimental allergic encephalomyelitis, Magn Reson Med, 40(1), 119-132. Streamtube models of white matter are created for each subject based on the major eigenvector of the diffusion tensor field and using the seeding and culling approach of Zhang et al. (2003) (Zhang, S., Demiralp, C., & Laidlaw, D. (2003), Visualizing diffusion tensor MR images using streamtubes and streamsurfaces, IEEE Transactions on Visualization and Computer Graphics, 9(4), 454-462) (incorporated by reference herein) which specifies the following input parameters: minimum threshold for linear anisotropy=0.1, minimum tube length=10 mm, minimum distance between tubes=2 voxels, and integration step size=1 mm. It was found that these parameters minimize the number of anatomically implausible fibers in regions of low anisotropy, while retaining linear structures in most of the white matter. The streamtube generation procedure produces a dense set of streamtubes that are then subjected to a distance-based culling process that removes similar (i.e., redundant) streamtubes to facilitate visual inspection and quantitative analysis. It is believed that the post-culling set of streamtubes is representative of all white matter features larger than one image voxel. The resultant models bear a close resemblance to known white matter structures such as cortical u-fibers, corpus callosum, superior longitudinal fasciculus, uncinate fasciculus, and cingulum bundles; other white matter structures are also easily identified. Except for models produced for a reproducibility study, all streamtube models used in group comparisons were generated with an input seeding that initiated a streamtube in every voxel (0.85 mm$^3$) of the volume. This seeding dimension was selected as an attempt to capture features as small as one-half of the intrinsic 1.7 mm resolution of the data.

Tract-of-Interest Selection

A method for interactive tract-of-interest selection that was implemented may be one similar to a volume of interest (VOI) approach described by Akers et al. (Akers, D., Sherbondy, A., Mackenzie, R., Dougherty, R., & Wandell, B. (2004), Exploration of the brain's white matter pathways with dynamic queries, Paper presented at the IEEE Visualization '04, San Antonio) (incorporated by reference herein) and bears a similarity to a more recent method published by Mori and colleagues (Jiang, H., van Zijl, P. C., Kim, J., Pearlson, G. D., & Mori, S. (2006). DTIstudio: Resource program for diffusion tensor computation and fiber bundle tracking, Comput Methods Programs Biomed, 81(2), 106-116) (incorporated by reference herein). Briefly, an interactive user interface is any interface that permits the operator to rotate and translate the streamtube model in all three axes using a computer mouse or other pointing device (see, for example, Akers et al. and/or Zhang et al.) This allows the operator maximum flexibility in viewing the model from different perspectives, and provides an ability to zoom in or out on specific structures of interest. The operator can then define three-dimensional box-shaped "volumes of interest". The size and shape of the boxes are controlled by the operator and can be dragged and placed anywhere in the streamtube model using the computer mouse or by inputting specific values for the box dimensions and location. There is no limit to the number of boxes that can be placed in a model. Once placed, a series of Boolean operations allows the operator to select only fibers that pass through a box, or that connect two or more boxes, and in this way to identify the tracts of interest (TOIs). TOIs selected in this manner may be manually edited using, for example, Boolean operators such as "not" to remove those streamtubes that have an anatomically incorrect or spurious trajectory. This method is exemplary, and in general any manual or automated method for selecting a subset of streamtubes of paths may be used to define a TOI.

Since the streamtube sets are three-dimensional and TOI selection is based on each participant's own anatomy, co-registration is not necessary. For each subject there was quantified the streamtube data for the whole brain white matter and three TOIs: transcallosal fibers, and the left and right cingulum bundles. TOI selection was performed by an experienced rater. In a non-limiting embodiment the transcallosal fibers were defined as being all streamtubes passing through the corpus callosum, and fibers that extended inferiorly through a plane defined by the inferior boundary of the splenium and rostrum in mid-sagittal view were removed from this TOI. While this conservative approach may remove anatomically correct streamtubes from the TOI (e.g., the tapetum), its use is preferred to ensure that anatomically implausible streamtubes were not included in the analysis. The left and right cingulum bundles were identified visually in the models and were segmented by the intersection of boxes placed in each bundle using a pre-specified algorithm for box placement. Given the potential errors that can occur in DTI fiber tracking (e.g., see Jiang et al. (2006)), a conservative approach to identifying and culling anatomically questionable fibers (e.g., those that seemed possibly anatomically spurious based on trajectory) is preferred.

Preferred Quantitative Tractography Metrics:

In accordance with the exemplary embodiments of this invention, a set of quantitative tractography metrics comprises the following members: 1) total length (TL); 2) total weighted length (TWL); 3) number of streamtubes (NS); 4) normalized total length (NTL); 5) normalized total weighted length (NTWL); 6) normalized number of streamtubes (NNS); and 7) average length (AL). These quantitative tractography metrics provide indirect markers as to the structural integrity of white matter TOIs. Table 1 shown in FIG. 1 briefly describes each quantitative tractography metric and its abbreviation. The metrics are defined conceptually and mathematically as follows.

Total length of a TOI is defined as:

$$TL = \sum_{\forall s \in S} L_s \qquad (1)$$

where $L_s$ is the length in millimeters of a single streamtube s contained within a set of streamtubes S in a given TOI. This quantitative tractography metric provides a coarse marker of the overall microstructural integrity of a TOI.

Total weighted length (TWL, also referred to as TWL_cl) weights the TL by an average linear anisotropy of the streamtubes comprising the TOI. Weighting by the average linear anisotropy provides different information about the integrity of the tract. For example, TWL may be sensitive to differences in tract integrity across groups (i.e., differences in the average linear anisotropy of the tract) that are insufficient to impact TL, but nonetheless reflect a disease state. TWL is defined as follows:

$$TWL = \sum_{\forall s \in S} (C_s \times L_s) \qquad (2)$$

where $C_s$ is the average linear anisotropy along a streamtube (i.e., linear anisotropy summed across all vertices used to generate a streamtube and divided by the number of vertices). One may expect TWL to be inversely correlated with TOI injury.

NS quantifies the number of streamtubes in a TOI:

$$NS = \|S\|. \qquad (3)$$

NS may provide useful information regarding white matter integrity that is not captured by the length metrics, and may be sensitive to white matter changes, particularly in shorter, denser tracts. NS may provide a compliment to the length metrics. For example, a lower TL value may occur because of broken fibers due to local minima in linear anisotropy, or to loss of fibers. In the former situation, the lower value of TL may be accompanied by a higher value of NS, whereas in the latter situation, both TL and NS may be decreased in value.

It is noted that the values of TL, TWL, and NS may likely be influenced by brain size, and thus may require further correction. Therefore, it is preferred to normalize these three metrics by the approximate intracranial volume. Normalizing by the intracranial volume is preferred to normalizing by brain volume as it provides a better index of brain size prior to the impact of age and pathology (e.g., see Bigler, E. D. (2004), Neuropsychological results and neuropathological findings at autopsy in a case of mild traumatic brain injury, J Int Neuropsychol Soc, 10(5), 794-806).

As an exemplary and non-limiting approach, the volume of the intracranial vault may be approximated by first defining a box enclosing the head. The box boundaries are determined in sagittal and coronal views of the T2 (i.e., b=0) volume and placed at the most superior, inferior, anterior, posterior, lateral points of the head (first slice in which any tissue is visualized). The inferior boundary is the foramen magnum. A measurement is then made of the volume of a mathematically generated three-dimensional ellipsoid circumscribed within the box. To account for extra-cranial tissue captured by the ellipsoid, the ellipsoid volume is multiplied for each individual by a correction factor based on normative intracranial volume estimates reported in a number of previous studies (e.g., the four studies reported by: Blatter, D. D., Bigler, E. D., Gale, S. D., Johnson, S. C., Anderson, C. V., Burnett, B. M., et al. (1995), Quantitative volumetric analysis of brain MR: Normative database spanning 5 decades of life, AJNR Am J Neuroradiol, 16(2), 241-251; Edland, S. D., Xu, Y., Plevak, M., O'Brien, P., Tangalos, E. G., Petersen, R. C., et al. (2002), Total intracranial volume: Normative values and lack of association with Alzheimer's disease, Neurology, 59(2), 272-274; Ge, Y., Grossman, R. I., Babb, J. S., Rabin, M. L., Mannon, L. J., & Kolson, D. L. (2002), Age-related total gray matter and white matter changes in normal adult brain. Part I: Volumetric MR imaging analysis, AJNR Am J Neuroradiol, 23(8), 1327-1333; and Whitwell, J. L., Crum, W. R., Watt, H. C., & Fox, N. C. (2001), Normalization of cerebral volumes by use of intracranial volume: Implications for longitudinal quantitative MR imaging, AJNR Am J Neuroradiol, 22(8), 1483-1489). The correction factor used is the ratio of a mean intracranial volume estimate calculated across these four studies to the mean brain box volume in healthy control and VCI subjects combined. Application of the correction factor brought the intracranial volume estimates in line with previously reported intracranial volume estimates derived with more exacting methods. Note that statistical parametric mapping (SPM) could be used in alternative embodiment.

The metrics TL, TWL, and NS are normalized by dividing these length metrics by the ratio of each participating subject's approximate intracranial volume to the average intracranial volume of all participating subjects. That is, the normalized total length (NTL), normalized total weighted length (NTWL), and normalized number of streamtubes (NNS) may be computed as follows:

$$NTL = \frac{TL}{V/\overline{V}}; \quad (4)$$

$$NTWL = \frac{TWL}{V/\overline{V}}; \quad (5)$$

$$NNS = \frac{NS}{V/\overline{V}}; \quad (6)$$

where $V$ is approximate intracranial volume, and $\overline{V}$ is the mean approximate intracranial volume for the healthy controls (HCs) and vascular cognitive impairment (VCI) subjects combined.

A seventh metric, AL, is a non-normalized measure of the average length of streamtubes in a TOI:

$$AL = \frac{TL}{NS}. \quad (7)$$

AL may provide different information than TL, possibly helping to discriminate between individuals with similar TL values but different white matter integrity. For example, AL may be useful to distinguish an individual with good white matter integrity, as reflected in long streamtubes, versus an individual with poor white matter integrity reflected by many shorter streamtubes.

It should be noted that one may additionally calculate a normalized AL and average values for the other length metrics by dividing each by NS. However, it may be desirable to omit these additional metrics in order to reduce the number of variables that need to be considered. Furthermore, it was found that these additional metrics (normalized AL and average values for the other length metrics) are highly correlated ($r>0.72$) with the metric in the numerator.

Note further that the exemplary embodiments of this invention are not limited to only the seven metrics discussed above and shown in FIG. 1. For example, one or both of TWL and NTWL may be weighted by FA, giving a total of nine metrics. For example, another metric that may be used is the total weighted length (TWL a), which is a TOI metric that is the TL weighted by an average fractional anisotropy of streamtubes comprising the TOI.

Note further that, in general, any appropriate scalar measure (e.g., FA and/or T2) may be used as a weighting factor. Thus, the seven metrics discussed herein and shown in FIG. 1 should not be considered as a limitation upon the use and practice of the exemplary embodiments of this invention.

Note further that the exemplary and non-limiting seven quantitative tractography metrics described above and shown in FIG. 1 are clearly related to one another but, as noted, are believed to have different implications for the nature of white matter integrity loss in various diseases. For example, inflammatory processes such as multiple sclerosis might reasonably alter diffusion anisotropy without causing fiber drop out or breaking. Accordingly, metrics that weight length by linear anisotropy may be used to capture important information that would be lost in non-weighted metrics. Alternatively, diseases associated with multiple subcortical lacunar infarction may actually produce more shorter tubes than might result from Wallerian degeneration of white matter fibers, such as may occur in Alzheimer's disease.

In summary, in that conventional MRI has limited specificity for characterizing the precise pathophysiological underpinnings of white matter changes the consideration of all seven of the quantitative tractography metrics described above and shown in FIG. 1 is desirable for quantifying the integrity of entire white matter TOIs.

Reproducibility

Two important factors potentially affect the reliability of the seven quantitative tractography metrics described above: A) the degree to which the streamtube generation algorithm yields consistent results; and B) the degree to which DTI acquisition parameters yield consistent results across repeated scans, where the head position is not identical.

Consistency of streamtube generation: Streamtubes are generated using algorithms that place randomly jittered seed points at regular intervals within the imaging grid. This jittering method reduces the likelihood of the output model being overly influenced by the grid, that is, it helps to ensure that no locations within the image volume are systematically under sampled. The cost for this small random jitter is that each run of the algorithm on a single dataset produces slightly different streamtube models, even if the input data and parameters are held constant. Such inconsistencies may have the potential to introduce error variance in the metrics which, if too great, could mask true group differences.

To address this concern, one may assess the consistency of the seven quantitative tractography metrics described above in multiple streamtube models derived from one dataset of a single healthy control subject. As an example, seven streamtube models were produced for each of three different seeding parameters that varied by coarseness (i.e., 1.7 mm$^3$, 0.85 mm$^3$, and 0.64 mm$^3$) for a total of 21 models. Other streamtube parameters were held constant as described previously. Assessed then was the coefficient of variance in the metrics across the seven whole brain models produced at each seeding parameter. This method allows one to determine the impact of both random jitter and different seeding parameters on the consistency of the metrics.

Consistency of data acquisition: The consistency of the set of quantitative tractography metrics was examined across data collected from a single healthy 45-year-old, right-handed control subject scanned on three different occasions.

An assessment was made of the stability of the set of quantitative tractography metrics vis-à-vis the streamtube generation algorithm in the dataset from the single healthy control. Seven streamtube models were produced for each of three different seeding parameters (21 total models). The metrics were measured in whole brain models. Coefficients of variance (COV) were calculated for each metric across the seven models for each seeding point. In the whole brain models, COV did not exceed 1.0% for either NS, TL, or TWL across seven models of a single brain produced at the three seeding densities of 1.7 $mm^3$, 0.85 $mm^3$ seeding, and 0.64 $mm^3$ (see Table 2, shown in FIG. 2). COVs are reported only for these three metrics, as they are indicative of the fundamental stability of the metrics as related uniquely to the underlying tractography data, and not to some other source of variance (i.e., ICV estimates).

The consistency of the quantitative tractography metrics with respect to different data acquisition was assessed in three datasets acquired from the single healthy control participant collected at three different time points. The test was limited to the same three metrics used to assess the impact of the streamtube algorithm, and a percent-difference is used as a measure of the discrepancy in the metrics across the three time points. The metrics were evaluated in a single streamtube model for each acquisition at a seeding parameter of 0.85 $mm^3$. COVs are presented in Table 2 (FIG. 2) and did not exceed 1.3% (for TWL).

These results demonstrate that the set of quantitative tractography metrics are stable with respect to subtle differences in the tractography models that could arise from jittering the seed points in the streamtube generation algorithm. The results also show that coarser seeding parameters are associated with somewhat greater variability in the metrics. This effect likely reflects inconsistency with which coarser algorithms find smaller features in a dataset. It can be noted all other metrics were measured in models generated with a seeding spacing of (0.85 $mm^3$) to match the voxel dimensions in the datasets. The results also demonstrate that the set of quantitative tractography metrics are stable across multiple datasets acquired at different times, and suggest that these metrics are robust to issues that can arise with serial data collection, such as differences in head placement in the scanner or subtle changes in the scanner itself.

Utility test of the metrics: To have utility for clinical purposes, the set of quantitative tractography metrics should acquire different values in patients with known white matter injury, as compared to those presumed to have normal white matter. This was addressed by comparing the values of the set of quantitative tractography metrics in a group of patients with known vascular white matter injury (i.e., vascular cognitive impairment or VCI) to values obtained from a group of demographically similar healthy control subjects. Patients with VCI typically have impairments that are greater than expected for age in the cognitive domains of processing speed, attention, and executive functioning, and somewhat milder deficits in memory.

Participants included 15 patients with VCI (mean age=59.24±11.73, range=40.10–79.22) and 18 healthy individuals (mean age=64.36±14.16, range=43.77–83.62) who served as control group. VCI was diagnosed by consensus at multidisciplinary case conferences considering data from clinical history, neurological exam, neuropsychological testing, and clinical brain MRI scans and using previous criteria specified by Erkinjuntti, T. (2002), Diagnosis and management of vascular cognitive impairment and dementia, J Neural Transm Suppl(63), 91-109. All VCI participants had impairments (i.e., performance falling more than 1.0 standard deviations below demographically-corrected means) on tests of executive cognitive functioning and/or memory and had MRI evidence of subcortical ischemic vascular disease (i.e., subcortical white matter hyperintensities on T2-weighted images and/or lacunar infarction on T1-weighted images) that was greater than expected for age. None had neuroimaging or clinical evidence of large vessel stroke. None met diagnostic criteria for dementia. In eight patients, VCI was due to CADASIL (cerebral autosomal dominant arteriopathy with subcortical infarction and leukoencephalopathy), a genetic form of subcortical ischemic microvascular disease with earlier onset than the more common non-genetic form. Healthy control participants were screened by self-report to ensure the absence of current clinically relevant neurological or psychiatric symptoms and all had normal global cognition as evidenced by scores of 25 or greater on the 30-item Mini-Mental State Exam. All data were collected as part of ongoing studies of DTI and cognitive and behavioral functioning in patients with disorders known to adversely impact white matter integrity.

As a preliminary step, an examination was made of the distributions of the variables for normality and homogeneity of variance. Multiple analysis of covariance (MANCOVA) (controlled for age) was used to test for significant differences in the metrics, and average FA, between the VCI and healthy control groups in whole brain models. It was expected that patients with VCI would have lower values on each of the set of quantitative tractography metrics metrics, as compared to healthy controls. The decision to use MANCOVA for this analysis reflected a desire to control for age. Alpha was set at 0.05 for each omnibus MANCOVA to guard against Type 1 error in the set of variables being compared. Group differences on the individual variables were considered only if the overall MANCOVA was significant. Since each MANCOVA controls for Type I error across the entire set of comparisons, and because there were two groups, no post-hoc testing was necessary. That is, the overall MANCOVA results arose from the same distributions as the pairwise comparisons for the individual metrics, and to apply further corrections for multiple comparisons may have the effect of over-correcting. All seven of the quantitative tractography metrics were retained in these analyses for thoroughness, since each potentially captures slightly different information about the integrity of a specific TOI.

TOI selection has a certain subjective element. Intra-rater reliability for transcallosal and the left and right cingulum bundles was assessed for the same three metrics based on nine datasets selected at random. The measurements were performed at least seven months apart and the rater performed no other ratings during this period. Intraclass correlation coefficients ranged from 0.69 to 0.91 for the transcallosal TOI, from 0.93 to 0.97 for the left cingulum, and 0.90 to 0.95 for the right cingulum bundle. Pearson bivariate correlations ranged from 0.88 to 0.93 for the transcallosal TOI, from 0.93 to 0.97 for the left cingulum bundle, and from 0.94 to 0.97 for the right cingulum bundle.

FIG. 3 shows sagittal views of whole brain streamtube models for one healthy control and one patient with VCI. In the healthy control group, correlations between age and each of the whole brain metrics were negative and significant with all r values ≧−0.57 and all p values≦0.013, except between age and ATL (r=−0.17; p=0.51). In the VCI group, age was not significantly correlated with any of the metrics.

A MANCOVA was conducted to evaluate group differences for the set of quantitative tractography metrics with age as a covariate. The overall model showed a non-significant effect of age (F=2.29; p=0.062) and a significant effect of group (F=2.95; p=0.022). After controlling for age, the VCI group had significantly lower values on all seven quantitative tractography metrics compared to the healthy controls (see Table 3 in FIG. 4). Effect sizes across the seven metrics were small (partial eta$^2$=0.14 to 0.25); observed power ranged from 0.61 to 0.87.

A Pearson bivariate correlation matrix revealed strong and statistically significant inter-correlations among all seven metrics with r values ranging 0.52 for ATL vs. NNS to 0.99 for TWL vs. NTWL (all p≦0.001).

Partial correlations, controlling for age, between whole brain NTWL and cognitive measures (TMT-A, TMT-B, and BNT) showed significant inverse correlations with TMT-A and TMT-B but not with BNT (see Table 4 in FIG. 5).

As can be appreciated, there is a high degree of collinearity among the metrics. This is not unexpected given that five of the seven measures are derived from TL, and because TL is clearly linked to NS. As such, one may use less that the full set of seven quantitative tractography metrics discussed above. However, as noted previously, there are conceptual differences between what aspects of white matter integrity each metric is capable of capturing. Therefore, it is preferred (although not a limitation upon the practice of this invention), to retain all metrics.

In whole brain streamtube models the set of quantitative tractography metrics were found to be significantly correlated with age in the healthy controls. This is not unexpected given prior research demonstrating significant associations between age and white matter volume, and age and microstructural integrity measured by DTI. The absence of significant correlations between age and the set of quantitative tractography metrics in the VCI group may reflect an alteration of the normal relationship between age and white matter integrity in the presence of subcortical vascular disease.

The VCI group had significantly reduced standing on all seven metrics compared to healthy controls, after controlling for age. This result is not at all unexpected given that the VCI group was selected for the presence of subcortical ischemic white matter changes on T2-weighted MRI. These results provide evidence that the set of quantitative tractography metrics are sensitive to white matter changes in a group of individuals with known vascular white matter injury.

The correlation analysis indicates that as NTL and NTWL decreased, the time to complete the TMT-A & B tasks increased. In contrast, the set of quantitative tractography metrics correlated very weakly with BNT and did not approach significance. These results provide additional support for the validity of the set of quantitative tractography metrics; specifically, that these metrics capture clinically relevant information about white matter integrity and its association with cognitive status.

Whole brain TOI metrics may be viewed as providing a "brute force" method for comparing groups on overall white matter integrity. At least one advantage of this approach is that the whole brain TOI provides a measurement of white matter integrity that takes into account white matter that appears both normal and abnormal on conventional MRI. Thus, the whole brain TOI metrics can provide more robust markers of white matter structural integrity than either volumetric measures of T2-lesions obtained from conventional images or scalar DTI measures taken from region-of-interest analyses in normal-appearing white matter. The whole brain approach, however, may not be as useful for testing hypotheses about the integrity of particular white matter pathways or their relation to cognitive and behavioral function. To explore the potential utility of the set of quantitative tractography metrics for answering such questions, a determination was made of whether the VCI and healthy control groups differed in the set of metrics for three discrete TOIs: 1) transcallosal fibers (TCF) and the 2) left and right cingulum bundles.

Figure 6:
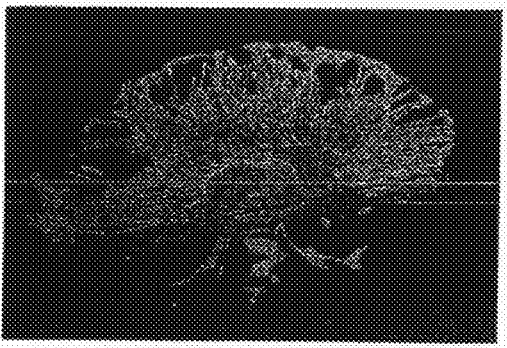
FIG. 6 depicts transcallosal fibers (TCF) for a 44-year-old healthy volunteer showing placement of volumes of interest.

Transcallosal fibers: FIG. 6 shows the TCF selection in a healthy control. The overall MANCOVA model revealed a non-significant effect of age (F=2.25; p=0.065); and a significant effect of group (F=3.39; p=0.012). After controlling for age, the VCI group had significantly lower values on all seven quantitative tractography metrics compared to the healthy controls (Table 3). Effect sizes across the seven metrics were small to moderate (partial eta$^2$=0.25 to 0.35); observed power ranged from 0.87 to 0.97. The group differences for all seven metrics were also significant when tested using the non-parametric Mann-Whitney U test (all p≦0.05). The results of the non-parametric analysis suggest that the violations of normality for these variables were not sufficient to invalidate the parametric MANCOVA procedure.

Figure 7:
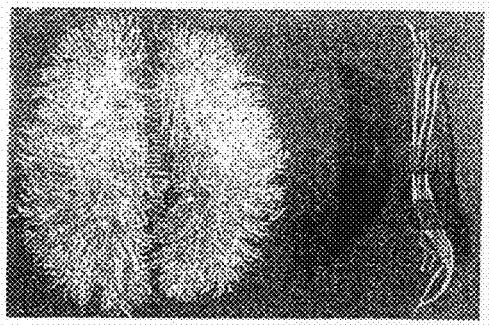
FIG. 7 depicts cingulum bundles segmented from a 76-year-old patient with VCI, where the left image shows placement of volumes of interest in axial view, and the right image shows a segmented cingulum bundle.

Cingulum Bundles: FIG. 7 shows an example of cingulum bundle selection in a patient with VCI.

For the left cingulum bundle, the overall model showed a non-significant effect of age (F=2.26; p=0.065) but the effect of group was significant (F=4.27; p=0.003). However, tests of between-groups effects controlled for age found no significant group differences for any of the metrics (see Table 3). No significant group differences across the metrics were found using Mann-Whitney U tests.

For the right cingulum bundle, the overall model was not significant for age or group. The means and standard deviations for each metric are reported in Table 3. No significant group differences across the metrics were found using Mann-Whitney U tests.

These results demonstrate that for transcallosal fibers, the VCI group has significantly lower standing on each of the seven metrics than the healthy control group suggesting poorer white matter integrity with both fewer and shorter streamtubes. This was not the case for the cingulum bundles where no significant differences were found between the groups. The results for the transcallosal fibers are not surprising as callosal and pericallosal T2-weighted hyperintensities are frequently observed in patients with VCI.

As can be appreciated, the use of the set of quantitative tractography metrics enables the detection in a reduction in white matter integrity (or more generally white matter impairment), such as in subjects with VCI as compared to healthy subjects, particularly in fibers passing through the corpus callosum.

The pattern of correlations with measures of cognitive functioning suggests that the set of quantitative tractography metrics capture clinically meaningful information. The use of the set of quantitative tractography metrics extend previous work on quantitative tractography, such as that reported in: Ciccarelli et al., 2003a and 2003b, Ding et al. (2003), Huang et al. (2005), and Parker et al., (2000), (2002a) and (2002b), and provide rather straightforward means of assessing the overall integrity of whole brain white matter or of specific white matter pathways.

Not surprisingly, there is considerable and significant shared variance among the metrics. This suggests that one metric may serve as a marker for the others from a statistical perspective. However, conceptually each metric provides somewhat unique information about the underlying white matter integrity. Therefore, and as was noted above, it may be preferred to utilize the full set of quantitative tractography metrics. However, it can be noted that the NTWL metric may capture the most information of all the metrics, as it is strongly correlated with the normalized number of streamtubes (NNS, r=0.90, p<0.001) indicating that this metric subsumes the number of streamtubes in a TOI. This is not surprising since all of the length-based metrics described herein implicitly contain information about the number of streamtubes in them. As such, it is within the scope of this invention to use the NTWL metric alone, or in combination with one or more of the other metrics described above.

The emphasis on length measures reflects the likelihood that many disorders affecting white matter produce local reductions in diffusion anisotropy that, in turn, cause the streamtube algorithm to terminate prematurely, produce tubes that are too short to be included in the model, or not run at all from a given seed point. All of these outcomes result in shorter and/or fewer streamtubes in a TOI of a patient with white matter disease, as compared to controls with healthy white matter. The extent of this effect, however, depends on the predetermined minimum linear anisotropy and length thresholds set in the algorithm for streamtube generation. The specific anisotropy and minimum length criteria ($\geqq 10$ mm) in the streamtube algorithm discussed above were chosen to limit the number of spurious, anatomically implausible fibers, while retaining a maximal number of anatomically plausible fibers. Moreover, it has been found that lower levels of anisotropy cause streamtubes to intrude on regions that are obviously grey matter. Thus, adjusting these parameters may impact the magnitude of the obtained set of metrics, but are unlikely to change the pattern of results.

Note further that the tractography algorithm is based on diffusion data acquired in 12 directions. However, more that 12 diffusion-encoding directions may be used to improve the anatomical accuracy of tractography models.

It is further noted that the use of linear anisotropy as the weighting factor in the TWL metric, rather than FA, should not be viewed as a limitation. For example, metrics weighted with FA have also been found to have utility. However, it is noted that in general FA does not differentiate between linear and planar anisotropy.

It is further noted that the intracranial volume estimate was defined by the boundaries of the intracranial vault, and this estimate may include a considerable amount of extracranial tissue and space and was vulnerable to certain sources of error. For example, rotations of the head relative to the scanner coordinate system would slightly alter the estimates. Clearly, more precise methods may be used. However, the goal is not to determine absolute intracranial volume, but rather to correct the length metrics for relative differences in intracranial vault size. For this purpose precise absolute measures of intracranial volume are not deemed to be necessary.

It is further noted that the normalization technique described above normalizes the length metrics with the intracranial volume estimate, and that the exemplary embodiments of this invention may use another normalization technique, such as by normalizing using some other measure.

The set of quantitative tractography metrics are clearly suitable for assessing the integrity of specific white matter pathways and the relationship to cognition and behavior. The metrics may have particular utility for gauging the magnitude of age-related reductions in white matter fiber length and the impact on cognitive functioning. For example, the total length of myelinated axons is reduced by as much as 47% in old age, with the greatest loss evident in small-diameter fibers, which myelinate later in life in frontal regions of the brain. Previous imaging studies of cognitive aging have relied on gross morphometry (e.g., white matter volume) and more recently standard DTI metrics of the microstructural integrity. These methods cannot address fiber length; rather they provide proxy measures of overall density and volume. In contrast, the use of the exemplary embodiments of this invention employs fiber tracking to quantify the length of myelinated fibers in the subcortical region of the brain, and may be used to test hypotheses that reductions in axonal length account for significant variance in cognitive aging.

The use of the set of quantitative tractography metrics may add incremental validity over and above other scalar DTI metrics (e.g.+fractional anisotropy) and conventional measures of white matter lesion volume based on T2-weighted images when discriminating between patients with and without white matter injury.

Since most tractography algorithms use information about the magnitude and vector of diffusion on a voxel-by-voxel basis, the basic principles underlying the set of quantitative tractography metrics can be expected to remain valid with other fiber tracking methods.

Figure 8:
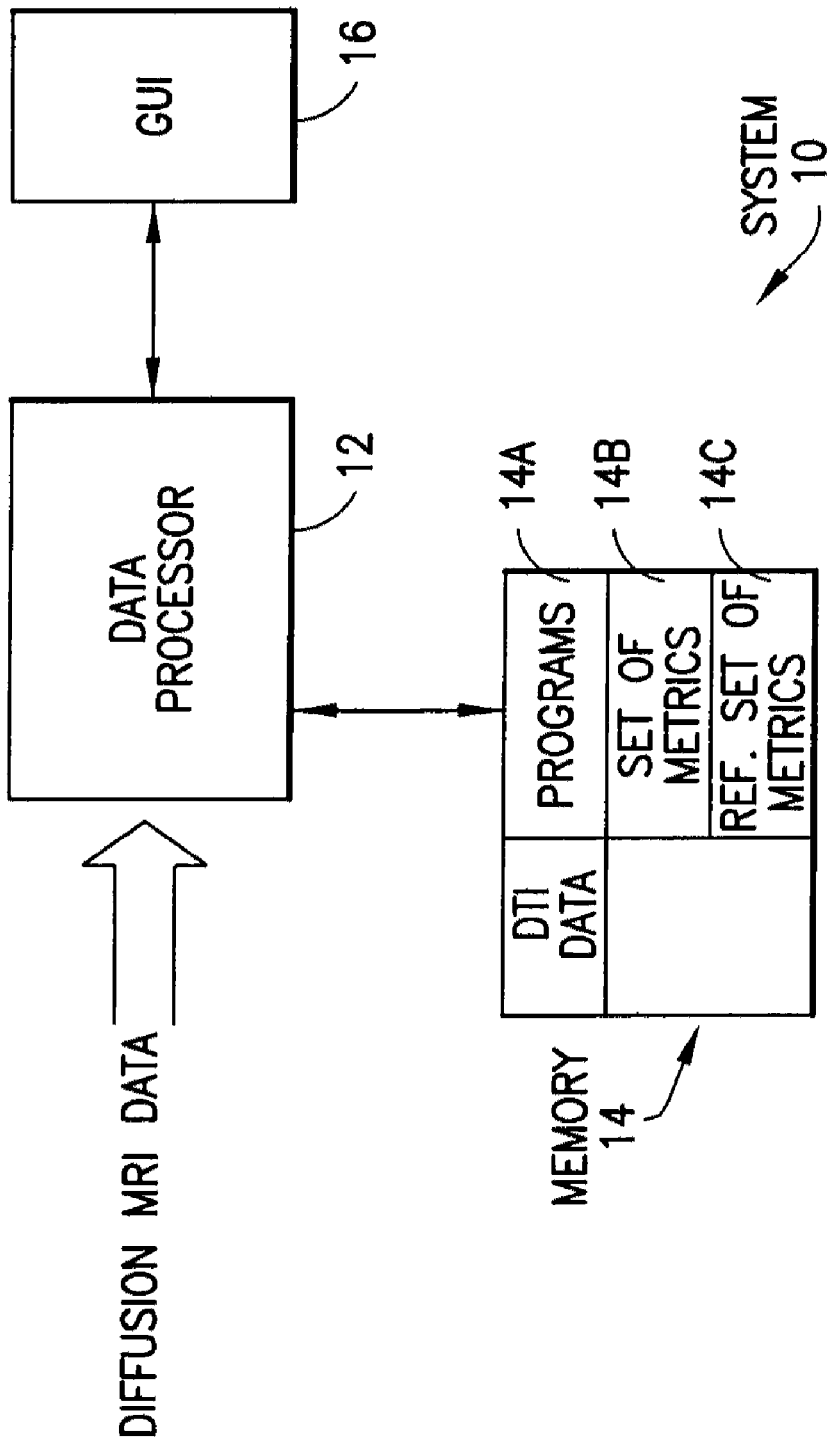
FIG. 8 is a block diagram of apparatus that is configured for use with and to implement the exemplary embodiments of this invention.

Reference is made to FIG. 8 for showing a block diagram of apparatus that is configured for use with the exemplary embodiments of this invention. In FIG. 8 a system 10 is configurable to detect a presence of cerebral white matter impairment, or more generally to characterize the white matter pathways in the brain of a subject. The system 10 includes a means, such as at least one data processor 12, that is responsive to data obtained by diffusion MRI imaging of a subject of interest for generating streamtubes representing white matter fibers in at least one tract of interest (TOI) in the brain of the subject of interest.

It is noted in this regard that the exemplary embodiments of this invention depend on tractographic results, but do not require that diffusion imaging produce a tensor field. As such, it may be preferred to use as a more general concept diffusion MRI and diffusion MRI data, as opposed to diffusion tensor imaging (DTI).

The data obtained by diffusion MRI imaging (D-MRI data) may be stored on some suitable memory medium 14, such as a disk, and the memory medium 14 may also store one or more computer software programs 14A to direct the operation of the data processor 12. The means for generating streamtubes may also include a user interface, such as a graphical user interface (GUI) 16 that can be used to visualize to an operator the D-MRI data and/or the generated streamtubes, and may also be used for identifying one or more tracks of interest alone or in combination with expert computer software that forms a part of the computer software programs 14A stored on the memory medium 14. The system 10 also includes means, such as one or more of the computer software programs 14A executed by the data processor 12, for determining the set of quantitative tractography metrics 14B based on the generated streamtubes, where the set comprises a plurality of members at least some of which are indicative of streamtube length. The system 10 also includes means, such as one or more of the computer software programs 14A executed by the data processor 12, for comparing at least some members of the determined set of quantitative tractography metrics to a reference set of quantitative tractography metrics 14C for indicating whether the subject of interest may have a cerebral white matter impairment.

As was discussed above, the members of the set(s) of quantitative tractography metrics 14B, 14C that are indicative of streamtube length can comprise a total length TL of a TOI metric, a total weighted length (TWL) of a TOI metric that is the TL weighted by an average linear anisotropy of streamtubes comprising the TOI, a normalized TL (NTL) metric, a normalized TWL (NTWL) metric, and a metric that is a non-normalized measure of the average length (AL) of streamtubes in the TOI, where the normalized metrics are normalized based on intracranial volume. As was also discussed above, the members of the set(s) of quantitative tractography metrics 14B, 14C that are not indicative of streamtube length comprise a number of streamtubes (NS) in a TOI metric, and a normalized NS (NNS) metric that is normalized based on intracranial volume.

Figure 9:
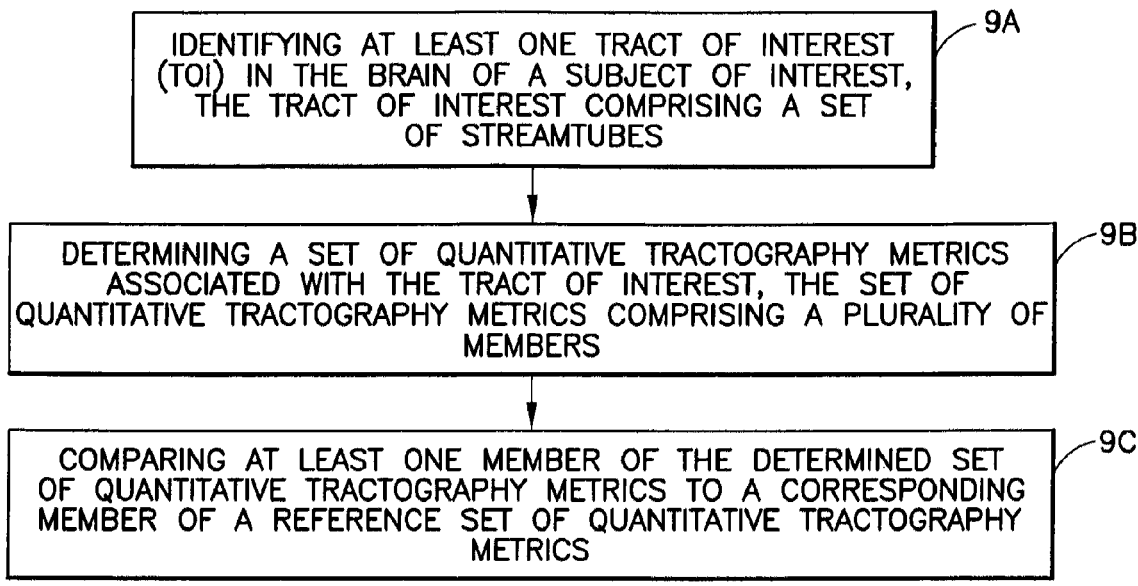
FIG. 9 is a logic flow diagram that is descriptive of a method, and execution of a computer program, in accordance with the exemplary embodiments of this invention.

Further in accordance with an exemplary embodiment of this invention, reference is made to FIG. 9 for showing a logic flow diagram that is descriptive of a method, and execution of the computer software programs 14A, in accordance with the exemplary embodiments of this invention. At Block 9A the method operates for identifying at least one tract of interest (TOI) in the brain of a subject of interest, the tract of interest comprising a set of streamtubes representing white matter fibers; (Block 9B) determining a set of quantitative tractography metrics associated with the tract of interest, the set of quantitative tractography metrics comprising a plurality of members; and (Block 9C) comparing at least one member of the determined set of quantitative tractography metrics to a corresponding member of a reference set of quantitative tractography metrics. A representative set of streamtubes may be assumed to be input to this process.

Figure 10:
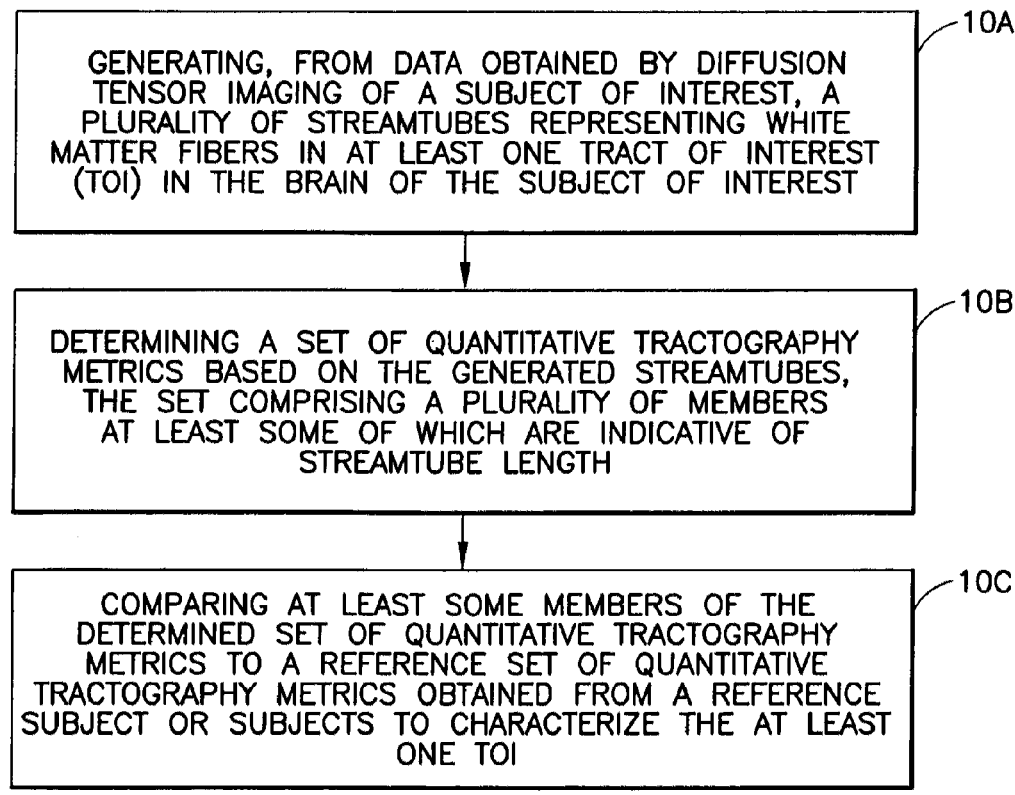
FIG. 10 is a logic flow diagram that is descriptive of a method, and execution of a computer program, in accordance with the exemplary embodiments of this invention.

Further in accordance with an exemplary embodiment of this invention, reference is made to FIG. 10 for showing a logic flow diagram that is descriptive of a method, and execution of the computer software programs 14A, in accordance with the exemplary embodiments of this invention. At Block 10A there is a step of generating, from data obtained by diffusion MRI imaging of a subject of interest, a plurality of streamtubes representing white matter fibers in at least one tract of interest (TOI) in the brain of the subject of interest. At Block 10B there is step of determining a set of quantitative tractography metrics based on the generated streamtubes, the set comprising a plurality of members at least some of which are indicative of streamtube length. At Block 10C there is a step of comparing at least some members of the determined set of quantitative tractography metrics to a reference set of quantitative tractography metrics obtained from a reference subject or subjects to characterize the at least one TOI.

While described above generally in the context of white matter impairments associated with aging, it should be appreciated that the exemplary embodiments of this invention may be used to detect a presence of white matter impairments originating from any number of causes, including injury and disease (such as HIV infection or stroke). In general, any exemplary embodiments of this invention have the potential to detect and/or indicate a presence or occurrence of any factor that has the potential to affect at least the length and possibly the numbers of paths in TOIs, which may be represented as streamtubes, in a subject of interest.

In addition, the use of the exemplary embodiments of this invention may be employed to generally characterize the white matter structure in a subject of interest, where the white matter structure may be correlated with, for example, an innate ability to perform some certain cognitive and/or motor task. For example, it may be found that the use of the set of quantitative tractography metrics has utility in identifying those individuals having a propensity towards mathematical reasoning and/or musical ability, or language ability, to name a few non-limiting examples.

As was noted above, tractography methods complement scalar methods by providing detailed information about the orientation and curvature of white matter pathways within the brain. Tractography methods utilize both the tensor eigenvalues and the eigenvectors to calculate trajectories in the direction of the fastest diffusion. The trajectories are then portrayed graphically using curved lines. As employed herein a collection of such curved lines may be considered to define a TOI, and may represent the whole brain. From the whole brain TOIs an expert (human and/or software expert) is enabled to identify a subset of these curves that represent a specific TOI, and from the specific TOI the set of quantitative tractography metrics can be calculated.

It should be noted that while certain of the exemplary embodiments have been generally described above in the context of comparing the set of quantitative tractography metrics derived from a subject of interest to a reference set of quantitative tractography metrics derived from one or more "healthy" control subjects, these exemplary embodiments may also be practiced by comparing the set of quantitative tractography metrics derived from the subject of interest to a reference set of quantitative tractography metrics derived from one or more subjects known to have a certain white matter impairment (e.g., from one or more individuals known to have Alzheimer's disease). In this non-limiting case there may be several reference sets of quantitative tractography metrics, individual ones of which are derived from some number of subjects having different stages or progressions of Alzheimer's disease (e.g., onset, medium, advanced). In this non-limiting case it may be possible to characterize the progression of the patient's Alzheimer's disease by determining with which reference set of quantitative tractography metrics the patient's set of quantitative tractography metrics most closely correlates with.

Further, it is within the scope of the use of the exemplary embodiments of this invention to compare the set of quantitative tractography metrics derived from the subject of interest with values for the set of metrics obtained from the same subject at an earlier point in time. In this manner it becomes possible to detect changes in white matter structures over time. That is, in this case the reference set of quantitative tractography metrics are derived from the same subject. For example, it is within the scope of this invention to compare, within the same subject, left and right brain hemispheres. In general, one may compare fiber bundles within the same person in the exact same dataset.

Various modifications and adaptations may become apparent to those skilled in the relevant arts in view of the foregoing description, when read in conjunction with the accompanying drawings and the appended claims. As but some examples, the use of other similar or equivalent streamtube generation algorithms, metrics, combinations of metrics and the like may be attempted by those skilled in the art. Further, it should be appreciated that in some cases only a single metric or measure need be calculated, especially in cases where a most relevant one has already been determined by earlier studies. Further still, and as was noted previously, the use of these exemplary embodiments is not limited to the brain, but may be used as well with muscle, and tendons, and the spinal cord, as non-limiting examples. Further, the use of these exemplary embodiments will find utility in other applications, such as in the study of plant life, where water and water-containing fluids are capable of diffusing through pathways.

However, all such and similar modifications of the teachings of this invention will still fall within the scope of this invention.

Furthermore, some of the features of the examples of this invention may be used to advantage without the corresponding use of other features. As such, the foregoing description should be considered as merely illustrative of the principles, teachings, examples and exemplary embodiments of this invention, and not in limitation thereof.

What is claimed is:

1. A method, comprising:
generating, from data obtained by diffusion MRI imaging of a subject of interest, a plurality of streamtubes representing white matter fibers in at least one tract of interest (TOI) in a brain image of the subject of interest;
determining a set of quantitative tractography metrics based on the generated streamtubes, the set comprising a plurality of members at least some of which are indicative of streamtube length; and
comparing at least some members of the determined set of quantitative tractography metrics to a reference set of quantitative tractography metrics obtained from at least one reference subject to characterize the at least one TOI, where the at least one reference subject comprises one of the subject of interest, at least one reference subject known to have a certain white matter impairment and at least one reference subject not known to have a certain white matter impairment.

2. The method of claim 1, where the members of the set of quantitative tractography metrics that are indicative of streamtube length comprise a total length TL of a TOI metric, a total weighted length (TWL) of a TOI metric that is the TL weighted by an average linear anisotropy of streamtubes comprising the TOI, a normalized TL (NTL) metric, a normalized TWL (NTWL) metric, and a metric that is a non-normalized measure of the average length (AL) of streamtubes in the TOI, where the normalized metrics are normalized based on intracranial volume, and where members of the set of quantitative tractography metrics that are not indicative of streamtube length comprise a number of streamtubes (NS) in a TOI metric, and a normalized NS (NNS) metric that is normalized based on intracranial volume.

3. The method of claim 1, performed as a result of the execution of at least one computer program stored on at least one computer readable memory medium.

4. A method to characterize white matter, comprising:
identifying at least one tract of interest (TOI) in the brain of a subject of interest, the tract of interest comprising a set of streamtubes representing white matter fibers;
determining a set of quantitative tractography metrics associated with the tract of interest, the set of quantitative tractography metrics comprising a plurality of members; and
comparing at least one member of the determined set of quantitative tractography metrics to a corresponding member of a reference set of quantitative tractography metrics.

5. A method, comprising:
generating, from data obtained by diffusion MRI imaging of a subject of interest, a plurality of streamtubes representing white matter fibers in at least one tract of interest (TOI) in a brain image of the subject of interest;
determining a set of quantitative tractography metrics based on the generated streamtubes, the set comprising a plurality of members at least some of which are indicative of streamtube length; and
comparing at least some members of the determined set of quantitative tractography metrics to a reference set of quantitative tractography metrics obtained from at least one reference subject to characterize the at least one TOI.

6. A method to characterize white matter, comprising:
identifying at least one tract of interest (TOI) in the brain of a subject of interest, the tract of interest comprising a set of streamtubes representing white matter fibers;
determining a set of quantitative tractography metrics associated with the tract of interest, the set of quantitative tractography metrics comprising a plurality of members; and
comparing at least one member of the determined set of quantitative tractography metrics to a corresponding member of a reference set of quantitative tractography metrics,
where a plurality of the members of the set of quantitative tractography metrics are length-based, and where at least one of the members of the set of quantitative tractography metrics is weighted using a scalar measure.

7. The method of claim 6, where one of the members of the set of quantitative tractography metrics is a total length TL of a TOI defined as:

$$TL = \sum_{\forall s \in S} L_s;$$

where $L_s$ is the length in millimeters of a single streamtube s contained within a set of streamtubes S in a given TOI.

8. The method of claim 7, where one of the members of the set of quantitative tractography metrics is a total weighted length (TWL) that weights the TL by an average linear anisotropy of streamtubes comprising the TOI defined as:

$$TWL = \sum_{\forall s \in S} (C_s \times L_s);$$

where $C_s$ is the average linear anisotropy along a streamtube.

9. The method of claim 8, where one of the members of the set of quantitative tractography metrics is a normalized TWL (NTWL), defined as:

$$NTWL = \frac{TWL}{V/\overline{V}};$$

where V is approximate intracranial volume of the subject of interest, and $\overline{V}$ is a mean approximate intracranial volume for subjects having no known white matter impairment and subjects having known white matter impairment, combined.

10. The method of claim 7, where one of the members of the set of quantitative tractography metrics is a normalized TL (NTL), defined as:

$$NTL = \frac{TL}{V/\overline{V}};$$

where V is approximate intracranial volume of the subject of interest, and $\overline{V}$ is a mean approximate intracranial volume for subjects having no known white matter impairment and subjects having known white matter impairment, combined.

11. The method of claim 6, where one of the members of the set of quantitative tractography metrics is a number of streamtubes (NS) in a TOI, defined as:

$$NS = \|S\|.$$

12. The method of claim 11, where one of the members of the set of quantitative tractography metrics is a normalized NS (NNS), defined as:

$$NNS = \frac{NS}{V/\overline{V}};$$

where V is approximate intracranial volume of the subject of interest, and $\overline{V}$ is a mean approximate intracranial volume for subjects having no known white matter impairment and subjects having known white matter impairment, combined.

13. The method of claim 11, where one of the members of the set of quantitative tractography metrics is a non-normalized measure of the average length (AL) of streamtubes in a TOI, defined as:

$$AL = \frac{TL}{NS}.$$

14. A system configurable to detect a presence of a white matter impairment, comprising a data processor connected with a non-transitory memory medium that stores computer software programs, where execution of at least one computer software program by the data processor results in the system performing operations that comprise processing data stored in the non-transitory memory medium representing white matter fibers in at least one tract of interest (TOI) in a brain image obtained from a subject of interest, where said processing comprises determining a set of quantitative tractography metrics based on the data, the set comprising a plurality of members, and comparing at least some members of the determined set of quantitative tractography metrics to a reference set of quantitative tractography metrics obtained from a subject or subjects either having or not having a certain white matter impairment, or obtained from the same subject of interest.

15. The system of claim 14, where execution of the at least one computer software program by the data processor results in at least some members of the set of quantitative tractography metrics being length-based, and where at least one of the members of the set of quantitative tractography metrics is weighted using a scalar measure.

16. The system of claim 14, where execution of the at least one computer software program by the data processor results in one of the members of the set of quantitative tractography metrics being a total length TL of a TOI, defined as:

$$TL = \sum_{\forall s \in S} L_s;$$

where $L_s$, is the length in millimeters of a single streamtube s contained within a set of streamtubes S in a given TOI.

17. The system of claim 16, where execution of the at least one computer software program by the data processor further results in one of the members of the set of quantitative tractography metrics being a total weighted length (TWL) that weights the TL by an average linear anisotropy of streamtubes comprising the TOI, defined as:

$$TWL = \sum_{\forall s \in S} (C_s \times L_s);$$

where $C_s$ is the average linear anisotropy along a streamtube.

18. The system of claim 17, where execution of the at least one computer software program by the data processor further results in one of the members of the set of quantitative tractography metrics being a normalized TWL (NTWL), defined as:

$$NTWL = \frac{TWL}{V/\overline{V}};$$

where V is approximate intracranial volume of the subject of interest, and $\overline{V}$ is a mean approximate intracranial volume for subjects having no known white matter impairment and subjects having known white matter impairment, combined.

19. The system of claim 16, where execution of the at least one computer software program by the data processor further results in one of the members of the set of quantitative tractography metrics being a normalized TL (NTL), defined as:

$$NTL = \frac{TL}{V/\overline{V}};$$

where V is approximate intracranial volume of the subject of interest, and $\overline{V}$ is a mean approximate intracranial volume for subjects having no known white matter impairment and subjects having known white matter impairment, combined.

20. The system of claim 14, where execution of the at least one computer software program by the data processor results in one of the members of the set of quantitative tractography metrics being a number of streamtubes (NS) in a TOI, defined as:

$$NS = \|S\|.$$

21. The system of claim 20, where execution of the at least one computer software program by the data processor further results in one of the members of the set of quantitative tractography metrics being a normalized NS (NNS), defined as:

$$NNS = \frac{NS}{V/\overline{V}};$$

where V is approximate intracranial volume of the subject of interest, and $\overline{V}$ is a mean approximate intracranial volume for subjects having no known white matter impairment and subjects having known white matter impairment, combined.

22. The system of claim 20, where execution of the at least one computer software program by the data processor further results in one of the members of the set of quantitative tractography metrics being a non-normalized measure of the average length (AL) of streamtubes in a TOI, defined as:

$$AL = \frac{TL}{NS}.$$

23. An apparatus to detect a presence of white matter impairment, comprising:

a data processor connected with a non-transitory memory medium that stores computer software programs, where execution of at least one computer software program by the data processor results in performing operations that comprise, responsive to data obtained by diffusion MRI imaging of a subject of interest, the data being stored in the non-transitory memory medium, generating streamtubes representing white matter fibers in at least one tract of interest (TOI) in a brain image of the subject of interest;

determining a set of quantitative tractography metrics based on the generated streamtubes, the set comprising a plurality of members at least some of which are indicative of streamtube length; and comparing at least some members of the determined set of quantitative tractography metrics to a reference set of quantitative tractography metrics for indicating whether the subject of interest may have a white matter impairment.

24. The apparatus of claim 23, where execution of the at least one computer software program by the data processor results in the members of the set of quantitative tractography metrics that are indicative of streamtube length comprising a total length TL of a TOI metric, a total weighted length (TWL) of a TOI metric that is the TL weighted by an average linear anisotropy of streamtubes comprising the TOI, a normalized TL (NTL) metric, a normalized TWL (NTWL) metric, and a metric that is a non-normalized measure of the average length (AL) of streamtubes in the TOI, where the normalized metrics are normalized based on intracranial volume.

25. The apparatus of claim 23, where execution of the at least one computer software program by the data processor results in members of the set of quantitative tractography metrics that are not indicative of streamtube length comprising a number of streamtubes (NS) in a TOI metric, and a normalized NS (NNS) metric that is normalized based on intracranial volume.

* * * * *